US007914979B2

(12) United States Patent
Chen et al.

(10) Patent No.: US 7,914,979 B2
(45) Date of Patent: Mar. 29, 2011

(54) STABLE AND FILTERABLE ENVELOPED VIRUS FORMULATIONS

(75) Inventors: Tzer-Fen Chen, McLean, VA (US); Jouhn-Wern Jang, Potomac, MD (US); Jeffrey A. Miller, Lincoln University, PA (US)

(73) Assignee: Wellstat Biologics Corporation, Gaithersburg, MD (US)

( * ) Notice: Subject to any disclaimer, the term of this patent is extended or adjusted under 35 U.S.C. 154(b) by 0 days.

(21) Appl. No.: 11/718,348

(22) PCT Filed: Nov. 4, 2005

(86) PCT No.: PCT/US2005/040149
§ 371 (c)(1),
(2), (4) Date: Oct. 23, 2007

(87) PCT Pub. No.: WO2006/052813
PCT Pub. Date: May 18, 2006

(65) Prior Publication Data
US 2008/0166784 A1  Jul. 10, 2008

Related U.S. Application Data

(60) Provisional application No. 60/625,349, filed on Nov. 5, 2004.

(51) Int. Cl.
*C12Q 1/70* (2006.01)
(52) U.S. Cl. .......................................................... 435/5
(58) Field of Classification Search .................. None
See application file for complete search history.

(56) References Cited

U.S. PATENT DOCUMENTS

| | | | |
|---|---|---|---|
| 4,338,335 A | 7/1982 | McAleer et al. | |
| 5,602,023 A | 2/1997 | Csatary | |
| 5,792,643 A * | 8/1998 | Herrmann et al. | 435/235.1 |
| 6,165,500 A | 12/2000 | Cevc | |
| 6,231,860 B1 | 5/2001 | Fanget et al. | |
| 6,258,362 B1 * | 7/2001 | Loudon et al. | 424/229.1 |
| 6,290,967 B1 | 9/2001 | Volkin et al. | |
| 2002/0156037 A1 | 10/2002 | Volkin et al. | |
| 2003/0044384 A1 | 3/2003 | Roberts et al. | |
| 2003/0103933 A1 | 6/2003 | Brody et al. | |
| 2008/0206281 A1 * | 8/2008 | Look et al. | 424/211.1 |

FOREIGN PATENT DOCUMENTS

| | | |
|---|---|---|
| DE | 299213 A7 | 4/1992 |
| EP | 0028563 A1 | 5/1981 |
| GB | 1274820 | 5/1972 |
| WO | 97/23238 | 7/1997 |
| WO | 00/62735 | 10/2000 |
| WO | 03/059292 A2 | 7/2003 |

OTHER PUBLICATIONS

Grande, et al., "Optimal conditions for the growth, purification and storage of the avian reovirus S1133", Journal of Virological Methods, vol. 102, pp. 53-54, 2000.
Yannarell, et al., "Stabilizing cold-adapted influenza virus vaccine under various storage conditions", Journal of Virological methods, vol. 102, pp. 15-25, 2002.
Gould, "Methods for Long-Term Virus Preservation", Molecular Biotechnology, vol. 13, pp. 57-66, 1999.
Barrett, et al., "Growth, Purification and Titration of Influenza Viruses, in Virology: A practical approach", Ed. B.W.J. Mahy; Raven Press Books, Chapter 6, pp. 119-145-146, 1985.
Blake, et al., :Virus Culture, Virology LabFax, Ed. D.R. Harper, BIOS Scientific Publishers Limited, Chapter 5, pp. 81-119, especially pp. 106-107, 1993.
Gelb, "Varicella-Zoster Virus", in Virology, Ed. B.N. Fields; Raven Press, Chapter 28, pp. 591-620, especially pp. 598, 1985.
Alexander, "Newcastle Disease in Laboratory Manual for the Isolation and Identification of Avian Pathogens", Chapter 27, 3rd ed., Purchase, et al., Kendal/Hunt, Iowa, p. 117, 1989.
Prestrelski, et al., "Separation of Freezing-and Drying-induced denaturation of Lyophilized Proteins using Stress-Specific Stabilization", Archives of Biochemistry and Biophysics, vol. 303, No. 2 pp. 465-473, 1993.
Guo, et al., "Tehalose expression confers desiccation tolerance on human cells", Nature Biotechnology, vol. 18, pp. 168-171, 2000.
Burke, et al., Formulation, Stability, and Delivery of Live Attenuated Vaccines for Human, Critical Reviews in Therapeutic Drug Carrier Systems, vol. 16, Issue 1, pp. 1-83, 1999.
Wade et al. eds., "Polyoxythylene Sorbitan Fatty Acid Esters", Handbook of Pharmaceutical Excipients, 2d ed., Amer. Pharm. Assoc., Washington, p. 375 (1994).
Howell, et al., "Effect on Sucrose Phosphate and Sorbitol on Infectivity of Enveloped Viruses During Storage", Journal of Clinical Microbiology, 18(3):658-662, Sep. 1983.

* cited by examiner

*Primary Examiner* — Ali R. Salimi
(74) *Attorney, Agent, or Firm* — Lewis J. Kreisler

(57) ABSTRACT

Envelope viruses (e.g. Newcastle disease virus (NDV)) are formulated for storage at moderately cold temperatures (e.g. −20° C.). The formulation is an aqueous solution containing the enveloped virus at a concentration of from $10^6$ PFU/mL to $10^{12}$ PFU/mL; and a non-reducing saccharide (e.g. sucrose). When the non-reducing saccharide is a disaccharide it is present in the solution at a concentration of from 5% (w/v) to 50% (w/v), and when it is a monosaccharide it is present in the solution at a concentration of from 2.5% (w/v) to 25% (w/v). The solution has an osmotic pressure of about 250 mOs or higher, and has a pH of from 5 to 10.

21 Claims, 1 Drawing Sheet

STABLE AND FILTERABLE ENVELOPED VIRUS FORMULATIONS

FIELD OF THE INVENTION

This invention pertains to the formulation of live therapeutic viruses and live virus vaccines.

BACKGROUND OF THE INVENTION

Only very limited examples for the stabilization of frozen liquid viable virus vaccines at −20° C. have been reported. Most of these did not employ purified viable enveloped virus (1, 2, 3, 4, 5). One of the major challenges to stabilizing enveloped virus at temperatures below the freezing point is preventing the physical disruption of structural and functional components (i.e. proteins, lipid bilayer and virus genome) during the freezing and storage stages. It has been reported that proteins are susceptible to denaturation (6), and lipid bilayers are prone to rupture during freezing (7). Several types of excipients have been reported to stabilize the structure of the lipid bilayer and proteins during freezing and in the frozen state (6, 7). These excipients include: polyols, saccharides, buffers, amino acids, and polymers.

The major tasks for stabilization of enveloped virus at temperatures below the freezing point are preventing the physical disruption of the virus's structural and functional components during both the freezing and storage stages. The enveloped virus components include: 1) the lipid bilayer envelope membrane; 2) the proteins coded by the viral genome, and 3) the single-stranded, or double stranded DNA or RNA genome.

In order to ensure stability during storage, stocks of infective virus have commonly been stored at ultra-low temperature (e.g. at ≦−60° C.) due to their complexity. Gould, E. A. ("Methods for long-term Virus Preservation", Molecular Biotechnology Vol. 13, pp. 57-66, 1999) teach that lipid enveloped viruses survive well at ultra low temperatures below −60° C. but that storage at −20° C. should only be used if "retention of virus infectivity is not essential". D. R. Harper described the storage conditions for a wide variety of non-enveloped and enveloped viruses ("Virology, Ed. D. R. Harper, BIOS Scientific Publishers Limited, Oxford, UK, 1993). In all cases, viruses must be stored at either −70° C. in liquid form or at 4° C. as a lyophile in order to retain infectivity. The storage conditions for liquid formulations of Newcastle disease virus are specifically mentioned as −70° C.

Yannarell et al ("Stabilizing cold-adapted influenza virus vaccine under various storage conditions", J. Virol. Meth. Vol. 102, pp. 15-25, 2002) describe conditions for storage of cold-adapted influenza virus vaccine at −20° C. using SPG, a mixture of sucrose, phosphate and glutamate (0.218M sucrose, 0.0038M monobasic potassium phosphate, 0.0072M dibasic potassium phosphate, 0.0049M potassium glutamate). Influenza virus prepared in allantoic fluid for intranasal administration was diluted 10% with a 10× solution of SPG. The final concentration of sucrose in this mixture was 7.5%. The presence of phosphate does not help to stabilize NDV while glutamate hinders sterile filtration and thus both compounds are detrimental to NDV preparation and storage at −20° C.

Parenteral administration adds an additional formulation issue. For safety reasons products for parenteral usage must be sterile filtered through a 0.2 μm filter, as terminal sterilization is not possible for viable virus preparations. Newcastle disease virions are pleomorphic but roughly spherical particles ranging in approximate size from 0.1 to 0.5 μm in diameter. The recovery rate of NDV filtered through a 0.2 μm sterile filter is formulation dependent and an important factor to be considered for developing a −20° C. liquid NDV formulation.

The factors affecting the ability of NDV to pass through a 0.2 μm sterile filter include the diameter of the virus, the filter pore size and the adsorptivity of NDV to the filter. The apparent diameter of NDV can be affected by: 1) The tonicity of the formulation; and 2) the surface charge of NDV, which may affect the molecular configuration and adsorption of proteins or nucleic acid on the surface of NDV in the presence of different buffers.

Adsorption of NDV to the filter membrane may also have a significant effect on the ability of the virus to sterile filter. Several factors may have impact on the surface properties of NDV and thus affect the adsorptivity of NDV to the filter. These factors include: 1) pH, 2) ionic strength, 3) surface interactions including hydrophobic or Van Der Waal interactions and ionic interactions and 4) the presence of surface-active agents such as surfactants.

BIBLIOGRAPHIC CITATIONS FOR BACKGROUND

1. Protocol "Methods for Long Term Virus Preservation", E. A. Gould, Molecular Biotechnology, Vol 13, 1999, pp 57-66.
2. T. Barrett, et al., "Growth, Purification and Titration of Influenza Viruses" in Virology: A practical Approach, Ed. B. W. J. Mahy; Raven Press Books, 1985, Ch. 6, pp. 119-146.
3. Virology Lab Fax: Ed. D. R. Harper; Bios Scientific Publishers Limited, 1993.
4. Lowrence D. Gelb, "Varicella-Zoster Virus" in Virology: Ed. B. N. Fields; Raven Press, 1985, Ch. 28, pp. 591-626.
5. Stabilizing cold-adapted influenza virus vaccine under various storage conditions: D. A. Yannarell et. al; Journal of Virological Methods; 102: 15-25, 2002.
6. Separation of Freezing- and Drying-induced denaturation of Lyophilized Proteins using Stress-Specific Stabilization, Prestrelski, et al., Archives of Biochemistry and Biophysics, Vol. 303, No. 2, June 1993, pp. 465-473.
7. Trehalose expression confers desiccation tolerance on human cells, N. Guo et al., Nature Biotechnology, Vol. 18 Feb. 2000, pp. 168-171.

SUMMARY OF THE INVENTION

This invention provides a method for stabilizing enveloped viruses for moderately cold temperature storage, comprising preparing an aqueous solution comprising: the enveloped virus at a concentration of from $10^6$ PFU/mL to $10^{12}$ PFU/mL; and a non-reducing saccharide. When the non-reducing saccharide is a disaccharide it is present in the solution at a concentration of from 5% (w/v) to 50% (w/v), and when it is a monosaccharide it is present in the solution at a concentration of from 2.5% (w/v) to 25% (w/v). The solution utilized in accordance with this invention has an osmotic pressure of about 250 mOs or higher, and has a pH of from 5 to 10.

This invention is based on the surprising finding that formulating enveloped viruses in an aqueous solution containing a non-reducing saccharide is an effective way of achieving both sterile filtration and long-term stability at moderately low temperatures.

DETAILED DESCRIPTION OF THE INVENTION

Figure 1:
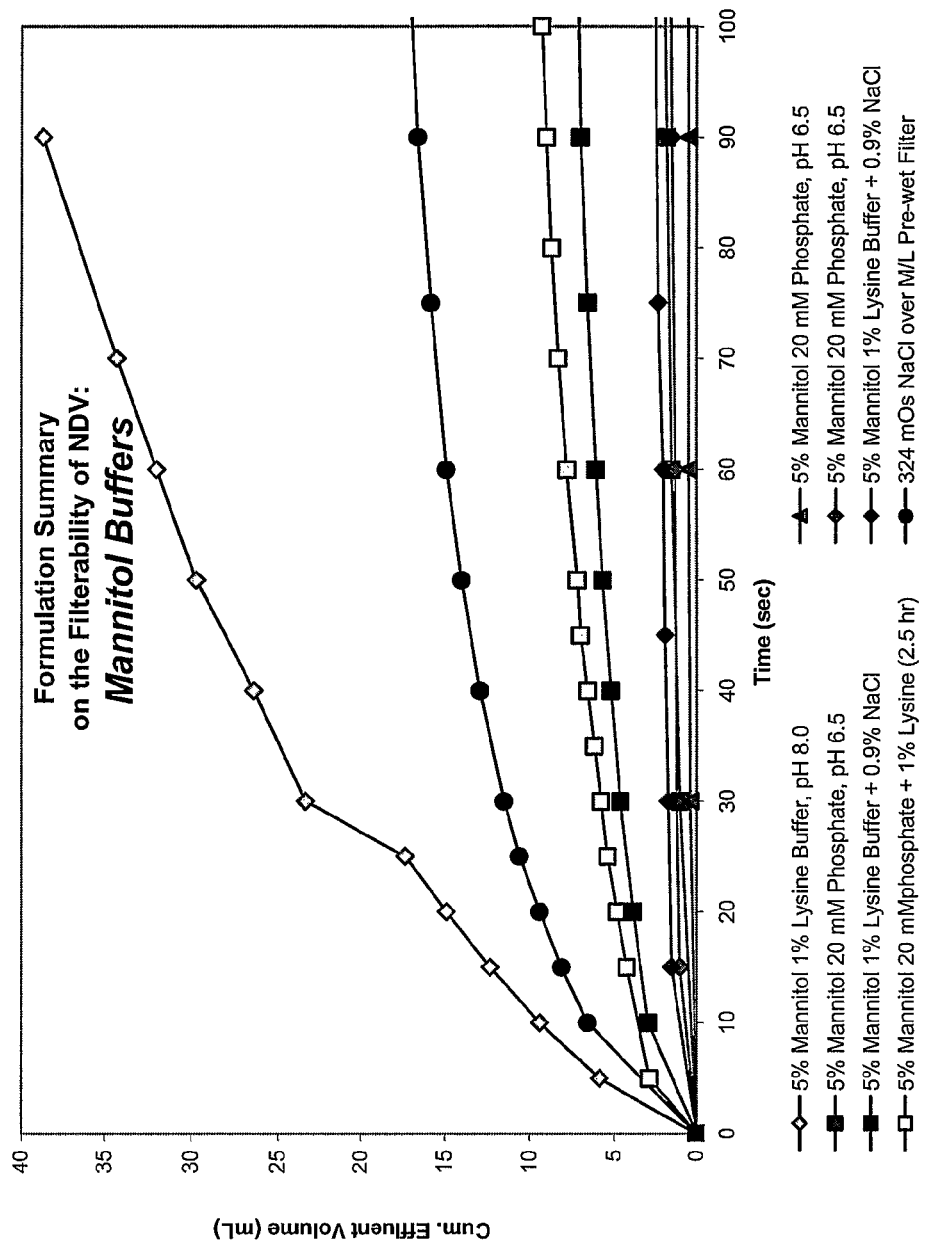
FIG. 1: The filterability of NDV in different buffers.

As used herein the transitional term "comprising" is open-ended. A claim utilizing this term can contain elements in addition to those recited in such claim. Thus, for example, the claims can read on treatment regimens that also include other therapeutic agents or therapeutic virus doses not specifically recited therein, as long as the recited elements or their equivalent are present.

As used herein "NDV" is an abbreviation for Newcastle disease virus. In accordance with this invention, when the virus is a Newcastle disease virus it can be of low (lentogenic), moderate (mesogenic) or high (velogenic) virulence. The level of virulence is determined in accordance with the Mean Death Time in Eggs (MDT) test. (Alexander, "Chapter 27: Newcastle Disease" in Laboratory Manual for the Isolation and Identification of Avian Pathogens, $3^{rd}$ ed., Purchase, et al. eds. (Kendall/Hunt, Iowa), page 117.) Viruses are classified by the MDT test as lentogenic (MDT>90 hours); mesogenic (MDT from 60-90 hours); and velogenic (MDT<60 hours).

As used herein "substantially no" amount of a given component or impurity means that the compound is present in the solution at a concentration of ten parts per million or less.

Given the inherent variability of the plaque forming unit assay, a virus is considered "stable" over a given time if less than 50% of infectivity is lost as measured by change in the amount of PFU/mL between an earlier time point and a later time point. Merely preserving enzymatic activity of individual viral proteins, without also preserving infectivity, is not considered to be the preservation of "stability" in the sense of this invention.

This invention utilizes an aqueous solution since water is essential in maintaining the three-dimensional structure and stability of enveloped viruses in liquid formulation.

Solutions in which the virus is too dilute are not desirable because the enveloped virus is less stable, whereas a high virus concentration does not seem to hurt stability during storage. In the freezing process, the enveloped virus will be concentrated into the interstitial region, in which condition the enveloped virus is considered to be in a highly concentrated state. In accordance with this invention the concentration of the enveloped virus from $10^6$ PFU/mL to $10^{12}$ PFU/mL, preferably from $1 \times 10^{10}$ PFU/mL to $7 \times 10^{10}$ PFU/mL.

Any enveloped virus can be formulated utilizing the aqueous solution in accordance with this invention. For example, paramyxoviruses such as Newcastle disease virus can be used. A mesogenic strain of Newcastle disease virus is currently preferred.

There are two important factors to be considered for protecting enveloped viruses from inactivation at moderately low temperatures (e.g. −20° C.): isotonicity in the liquid state and preventing denaturation of the proteins and the rupture of the lipid membrane during freezing. If the osmotic pressure is much lower than the isotonic point, it may cause the viral membrane to burst. High osmotic pressure doesn't seem to affect the stability of enveloped viruses during storage. In accordance with this invention an osmotic pressure of about 250 mOs or higher is suitable. Preferably the osmotic pressure is about 300 mOs. When the concentration of saccharide in the solution is much below 10% (w/v) it may be necessary to add other excipients to achieve a desirable osmotic pressure.

The other important factor that may affect the stability is the rupture of the structure and functional components during freezing and storage. Non-reducing saccharides, especially disaccharides are most effective in protecting enveloped viruses from inactivation during freezing. Without intending to be limited by mechanism, it is believed that the protection occurs by preventing the denaturation of the three dimensional structure of proteins and the rupture of the lipid bilayer structure. Non-reducing saccharides can also be used to adjust the osmotic pressure in the final formulation. In contrast, the reducing saccharide lactose did not show the same stabilizing effect. Any non-reducing saccharide can be utilized in the solution of this invention. When the saccharide is a disaccharide, it is present in the solution at a concentration of from 5% (w/v) to 50% (w/v). In a specific embodiment the disaccharide is present at a concentration of from 7.5% (w/v) to 15% (w/v). In a preferred embodiment the disaccharide is present at a concentration of from 10% (w/v) to 20% (w/v), more specifically about 10% (w/v). Examples of suitable disaccharides include sucrose or trehalose. When the saccharide is a monosaccharide, it is present in the solution at a concentration of from 2.5% (w/v) to 25% (w/v); preferably from 4% (w/v) to 7% (w/v), more preferably about 5% (w/v).

In accordance with this invention the solution can optionally further contain lysine (L-lysine and D-lysine are suitable) or arginine at a concentration from 0.1% (w/v) to 5% (w/v) or lysine and arginine at a combined concentration from 0.1% (w/v) to 5% (w/v). Preferably the concentration of lysine and/or arginine is about 1% (w/v).

Stability of the virus is affected by the pH. In accordance with this invention the solution can have a pH from 5 to 10, preferably from 6.5 to 9, more preferably from 7 to 9, more specifically about 7.5.

Various compounds have a negative effect on stability, filterability, or both, and their presence in the solution should be minimized. For optimal stability, the solution in accordance with this invention should contain substantially no reducing agents (e.g. reducing saccharides, Cysteine) or antioxidants (e.g. EDTA, ascorbic acid). Certain other compounds are less deleterious and, accordingly, need not be excluded entirely. For example it is acceptable for the solution utilized in accordance with this invention to contain up to 0.1% (w/v) Sodium chloride; 1% (w/v) Dextran; 0.5% (w/v) Mannitol; 0.1% (w/v) Sorbitol; 0.01% (w/v) TWEEN (polysorbate); 0.01% (w/v) Glutamate; 0.5% (w/v) polyethylene glycol; 0.1 mM Calcium chloride; 0.5% (w/v) Phosphatidyl choline; 0.05% (w/v) Glycine; and 0.01% (w/v) phosphate. Nevertheless it is preferable for the solution to contain substantially no Sodium chloride, Dextran, Mannitol, TWEEN (polysorbate), Glutamate, polyethylene glycol, Calcium chloride, Phosphatidyl choline, Glycine, and phosphate. Glycine as well as negatively charged buffers such as glutamate or phosphate buffers is not good for sterile filtration and recovery.

When the solution is to be administered parenterally it should be sterile. Sterility is not crucial for topical or oral administration. It can, and preferably should, be sterilized prior to low temperature storage with a pharmaceutical grade sterilizing filter. The preferred method for sterilization is size-filtration using a filter having a size larger than the effective size of the enveloped virus but smaller than bacteria. A 0.2 micron sterile filter is preferred. Usually the viscosity of the solution increases with concentration, which can make it harder for NDV to be filtered. To obtain a good virus recovery rate during sterile filtration the pressure should preferably be kept within 10 to 15 psi. With high viscosity and low pressure settings, it can be very difficult to filter enveloped viruses. The problem with high viscosity can be overcome by using aseptic mixing after sterile filtration of the virus. To avoid high viscosity it is preferable not to use high concentrations of excipients. For example, dextran, a glucose based polymer, can affect the filtration and recovery of virus during final filtration.

Although it was previously believed that liquid formulations of enveloped viruses are stable only at ultra low temperatures such as −60° C. or −70° C., surprisingly it has been found that enveloped viruses formulated in accordance with this invention are stable for long periods of time at −20° C. For example, enveloped viruses formulated as in this invention are stable at temperatures from −4° C. to −30° C., preferably −10° C. to −30° C., more preferably from −15° C. to −25° C., still more preferably at −20° C. Storage at about −20° C. is convenient. The ability to maintain stability at −20° C. will make it possible for a therapeutic product to be stocked in hospitals and pharmacies, which typically have −20° C. freezers but usually do not have −70° C. freezers. Moreover, because traditional container closures maintain better flexibility at −20° C. than at −70° C., sterility maintenance and therefore patient safety is assured by storage at −20° C. Utilizing the method of this invention, enveloped viruses are stable for 6 months, 12 months, 24 months or longer.

The invention will be better understood by reference to the following examples, which illustrate but do not limit the invention described herein. In the following examples, the NDV is a triple-plaque purified MK107 strain, which is an attenuated (mesogenic) version of Newcastle disease virus, described more fully in International Patent Publication WO 00/62735, published Oct. 26, 2000 (Pro-Virus, Inc.). The entire content of WO 00/62735 is hereby incorporated herein by reference.

EXAMPLES

ML is defined as 5% (w/v) mannitol/1% (w/v) lysine at pH 8.0

Example 1

Stability of NDV in 5% (w/v) Mannitol/1% (w/v) Lysine Solution

NDV was derived from the mesogenic Newcastle disease virus strain Mass-MK107 by triple plaque purification and produced by inoculation of the virus in the allantoic fluid cavity of 10 days old embronated chicken eggs. After incubation at 36° C. for 2 days, the eggs were chilled and the allantoic fluid harvested. The harvested allantoic fluid was diafiltered with 5% (w/v) D-mannitol and 1% (w/v) L-lysine, pH 8.0 buffer (ML), clarified and purified by tangential flow filtration and size exclusion chromatography to a concentration of 1 to 4 E+10 PFU/mL, aliquoted and stored at −20° C. NDV titer was measured by plaque assay and expressed as the amount of infectious NDV plaque forming units (PFU) per milliliter. For this assay, human HT1080 fibrosarcoma cells were seeded into tissue culture plates and grown to confluence. The growth medium was removed, the cell monolayers washed with medium and 0.5 mL of NDV sample added. The plates were incubated by rocking for 90 minutes at 37° C. and 5% $CO_2$. The monolayers were washed as described, and 3 mL of semi-solid agar medium overlaid onto each well. The cultures were incubated for 48 hours at 37° C. and 5% $CO_2$. The cell monolayers were stained with neutral red, the plaques counted, and the virus titers determined, PFU/mL. The results (Table I) indicated that NDV stored at −20° C. in 5% mannitol/1% lysine was not stable losing in average greater than 80% activity. Stability was expressed as the percent of titer remaining with respect to the time zero titer.

TABLE I

Stability of NDV formulated in 5% D-mannitol (w/v) and 1% L-lysine (w/v) at −20° C.

| | % Activity Remaining | | | | |
|---|---|---|---|---|---|
| Lot # | 4 Month | 8 Month | 12 Month | 18 Month | 24 Month |
| 1 | 26 | NT* | 17 | NT | NT |
| 2 | 18 | 15 | 9 | NT | NT |
| 3 | 11 | 6 | 0.3 | 0.9 | 1.4 |

*NT: Not Tested

Example 2

Stability of NDV in 10% (w/v) Sucrose Solution

NDV was prepared by method described in example 1, buffer exchanged into a 10% (w/v) sucrose solution by tangential flow filtration and size exclusion chromatography, aliquoted and stored at −20° C. Stability was measured by plaque assay as described in example 1. The results (Table II) indicated that NDV stored at −20° C. in 10% (w/v) sucrose was stable for up to 24 months.

TABLE II

Stability of NDV 10% (w/v) Sucrose formulation at −20° C.

| | % Activity Remaining | | | | |
|---|---|---|---|---|---|
| Lot # | 3 Month | 6 Month | 12 Month | 18 Month | 24 Month |
| 1 | 100 | 100 | 82 | 91 | 100 |
| 2 | 83 | NT | 96 | NT | NT |
| 3 | 79 | 93 | 72 | NT | NT |

*NT: Not Tested

Example 3

Stability of NDV in 10% (w/v) Sucrose Solution Containing Other Excipients

NDV was prepared by the method described in example 1 and buffer exchanged into a 10% (w/v) sucrose solution by tangential flow filtration and size exclusion chromatography. Separate formulations of NDV in 10% (w/v) sucrose containing an amino acid were prepared by the addition of either L-lysine, L-glycine or L-glutamic acid to a final concentration of 1% (w/v). The formulations were aliquoted and stored at −20° C. Stability was measured by plaque assay as described in example 1. The results (TABLE III) indicated that NDV stored at −20° C. in 10% (w/v) sucrose containing 1% lysine, 1% glycine or 1% glutamic acid was stable for up to 14 months.

TABLE III

Stability of NDV in 10% (w/v) sucrose containing amino acids at −20° C.

| | % Activity Remaining | |
|---|---|---|
| NDV/buffer | 4 Months | 14 Months |
| 10% Sucrose/1% (w/v) L-Lysine (pH 6.5) | 100% | 138% |
| 10% Sucrose/1% (w/v) L-Glycine (pH 6.5) | 105% | 115% |
| 10% Sucrose/1% (w/v) L-Glutamic Acid (pH 7.9) | 100% | 107% |

Example 4

Stability of NDV in Other Buffer Solutions

NDV was prepared by the method described in example 1. Portions of the NDV sample were buffer exchanged into different formulations including: 5% (w/v) mannitol/1% (w/v) L-lysine/2% (w/v) Gelatin hydrolysate, 10% (w/v) trehalose/1% (w/v) L-lysine, 200 mM Sodium acetate in 5% (w/v) mannitol/1% (w/v) lysine and 2% human serum albumin (HSA) in 5% (w/v) mannitol/1% (w/v) lysine, aliquoted, and stored at −20° C. Stability was measured by plaque assay as described in example 1. The addition of 2% (w/v) gelatin hydrolysate to NDV prepared in 5% (w/v) mannitol/1% (w/v) L-lysine significantly improved stability as compared to NDV prepared in the mannitol/L-lysine formulation (See example 1) while the addition of 2% HSA provided a more modest level of protection.

TABLE IV

Stability of NDV formulation in buffers containing gelatin hydrolysate, HSA, Na Acetate, and trehalose at −20° C.

| | % Activity Remaining | | | | |
|---|---|---|---|---|---|
| NDV/Buffer | 4 Months | 8 Months | 12 Months | 18 Months | 24 Months |
| 2% Gelatin Hydrolysate ML | 78 | 71 | 64 | 66 | 80 |
| 10% Trehalose/1% Lysine | 35 | NT | 29 | NT | NT |
| 200 mM Sodium Acetate ML | 67 | 52 | 37 | NT | NT |
| 2% HSA/ML | 65% | 70% | 51% | 43% | NT |

Example 5

Stability of NDV in Dextran Buffers at −20° C.

NDV was prepared by the method described in example 1. Portions of the NDV sample were buffer exchanged into different formulations including: 0.9% (w/v) NaCl/5% (w/v) Dextran and 10% (w/v) trehalose/20% (w/v) dextran. Dextran was found to provide a moderate level of protection to NDV (Table V) when NDV was stored at −20° C.

TABLE V

Stability of NDV in Dextran buffers at −20° C.

| | % Activity Remaining | | | | |
|---|---|---|---|---|---|
| Formulation | 3 Months | 6 Months | 9 Months | 12 Months | 18 Months |
| NDV 0.9% NaCl/5% Dextran | 61% | 55% | 52% | NA | 22% |
| NDV 10% Trehalose/ 20% Dextran (70K) | 64% | 61% | 50% | 26% | 17% |

Example 6

Stability of NDV in Other Buffer Solutions

NDV was purified by the method described in example 1, buffer exchanged into different buffers (See example 4 and 5), aliquoted and stored at −20° C. Stability was measured by plaque assay as described in example 1. The results (Table VI) indicated that NDV prepared in these buffers described in Table VI were not stable when stored at −20° C.:

TABLE VI

NDV in Buffers showing poor stability at −20° C.

| | % Activity Remaining | | |
|---|---|---|---|
| Formulation | 4M | 8M | 12M |
| 5% (w/v) Mannitol/1% (w/v) L-Lysine | 18% | 15% | 9% |
| 0.1% (w/v) TWEEN (polysorbate)/ML | <1% | NT | NT |
| 10% (w/v) Lactose solution | <1% | NT | NT |
| 2% (w/v) Gelatin/5% (w/v) Mannitol/1% (w/v) Lysine | 13% | NT | NT |
| 1% (w/v) Arginine/5% (w/v) Mannitol solution | 2.3% | NT | NT |
| 1% (w/v) Glutamic Acid/5% (w/v) Mannitol | <1% | NT | NT |
| 5% (w/v) PEG/5% (w/v) Mannitol/1% (w/v) Lysine | 3.7% | NT | NT |
| 10 mM CaCl$_2$/ML | 6% | NT | NT |
| 5% PhosphatidylCholine/ML | 14% | NT | NT |
| 1% Glycine/5% (w/v) Mannitol | 5% | NT | NT |
| 0.05% EDTA/5% (w/v) Mannitol/1% (w/v) Lysine | 31% | 17% | NA |

*NT: Not Tested

Example 7

Sterile Filtration of NDV Prepared in Mannitol

NDV in 5% (w/v) mannitol/1% (w/v) lysine was prepared as described in Example 1. A portion was diafiltered (how) into 5% (w/v) mannitol. Dextran was added to another portion of NDV ML to prepare a sample of NDV in ML containing 10% (w/v) dextran. These samples were tested for their ability to undergo sterile filtration by passing approximately 30 mL of each sample sequentially through a 0.45 um Sartobran™ pre-filter and a 0.22 um Sartobran™ filter under 15 psi. The filters were pre-wetted with ML buffer. The filtrants from each sample were collected and analyzed by plaque assay for the total amount of recovered viral plaque activity (PFU) as described in Example 1. NDV prepared in ML buffer or in 5% (w/v) mannitol was readily filtered while NDV prepared in ML buffer containing 10% (w/v) dextran did not pass through the filter appreciably (Table VII).

TABLE VII

Summary of Filtration Studies for NDV
Containing Mannitol/Lysine/Dextran

| Formulation | Total Recovery (Percent Load, Normalized) |
|---|---|
| ML | 82 ± 17 |
| 5% (w/v) Mannitol | 83 ± 17 |
| 10% (w/v) Dextran/5% (w/v) Mannitol/1% (w/v) Lysine | 4 ± 3 |

Example 8

Sterile Filtration of NDV Mannitol Buffer Containing Lysine/Phosphate/NaCl

NDV was prepared as described in example 1, exchanged into the buffers described in FIG. 1 and tested for their ability to undergo sterile filtration as described in example 7. Filters were prewetted with buffer used in the formulation. For each formulation the volume of NDV buffer that passed through the filter was collected and the accumulated volume calculated. NDV prepared in 5% (w/v) mannitol/1% (w/v) lysine filtered well. NDV prepared in 324 mOs NaCl filtered somewhat but NDV did not sterile filtered well when prepared in 5% (w/v) mannitol containing 1% (w/v) L-lysine, 20 mm phosphate or 5% (w/v) mannitol/1% (w/v) lysine containing 0.9% NaCl or 20 mM phosphate.

Example 9

Sterile Filtration of NDV prepared in buffer containing 10% (w/v) Sucrose or 10% (w/v) Trehalose NDV samples were prepared as described in Example 1 and diafiltered into 10% (w/v) sucrose or 10% (w/v) trehalose. From these solutions additional samples of NDV containing 10% (w/v) sucrose/1% L-lysine, 10% (w/v) sucrose/1% L-lysine/10% (w/v) dextran, and 10% (w/v) trehalose/1% L-lysine were prepared by the addition of the respective components. The samples were tested for their ability to undergo sterile filtration as described in Example 6. NDV prepared in 10% (w/v) sucrose, 10% (w/v) sucrose/1% (w/v) L-lysine or 10% (w/v) trehalose sterile filtered with a very good recovery rate. NDV prepared in 10% (w/v) trehalose/1% (w/v) L-lysine filtered with a reasonable recovery rate, while NDV prepared in 10% (w/v) sucrose/1% (w/v) L-lysine/10% (w/v) dextran sterile filtered poorly (Table VIII).

TABLE VIII

Summary of Filtration Studies for NDV Containing
Sucrose/Trehalose/Lysine/Dextran

| Formulation | Total Recovery (Percent Load, Normalized) |
|---|---|
| 10% Sucrose | 69 ± 7 |
| 10% Sucrose/1% Lysine | 83 ± 3 |
| 10% Trehalose | 74 ± 3 |
| 10% Trehalose/1% Lysine | 60 ± 7 |
| 10% Dextran/10% Sucrose/1% Lysine | 11 ± 1 |

Example 10

Sterile Filtration of NDV Prepared in 10% Sucrose Containing 1% L-Lysine, 1% L-Glutamate or 1% L-Glycine NDV samples were prepared as described in Example 1 and diafiltered into 10% (w/v) sucrose. This material was separated into four portions. L-lysine, L-glutamate, or L-glycine was added to each of three of these portions to produce samples containing 10% (w/v) sucrose and 1% (w/v) L-lysine, L-glutamate, or L-glycine. These samples were tested for their ability to undergo sterile filtration as described in Example 6. NDV prepared in 10% (w/v) sucrose or 10% (w/v) sucrose containing 1% L-lysine were readily filtered while NDV prepared in 10% (w/v) sucrose containing 1% (w/v) L-glutamate or glycine filtered marginally (Table IX).

TABLE IX

Summary of Filtration Studies for NDV Containing
Sucrose/Lysine/Glutamic Acid/Glycine

| Formulation | Total Recovery (Percent Load, Normalized) |
|---|---|
| 10% Sucrose | 66 ± 11 |
| 10% Sucrose/1% Lysine | 55 ± 16 |
| 10% Sucrose/1% Glutamic Acid | 35 ± 5 |
| 10% Sucrose/1% Glycine | 25 ± 1 |

Example 11

Stability of NDV in 10% Sucrose/Lysine in Different pH

NDV was prepared by methods described in example 1 and buffer exchanged into 10% (w/v) sucrose. Test samples of NDV/10% sucrose solution at different pH's were prepared by adding pH adjusted sucrose/lysine buffer (different pH's) and stored at −20° C. Stability samples were tested by plaque assay as described in example 1. The results indicated that NDV/10% sucrose solution is more stable in the range of pH 7.3 to pH 8.8 than at lower pH.

TABLE X

Stability of NDV formulated in 10% sucrose (w/v)/1% lysine (w/v) at different pH's at −20° C.

| Formulation | % Activity Remaining | | | |
|---|---|---|---|---|
| (0-time: Oct. 22, 2005) | 6 Month | 6 Month | 9 Month | 12 Month |
| NDV 10% Sucrose Control (pH 5.7) | 41% | 26% | 35% | 29% |
| NDV Suc/1% Lysine pH 5.3 | 50% | 38% | 28% | 42% |
| NDV Suc/1% Lysine pH 5.7 | 68% | 71% | 52% | 39% |
| NDV Suc/1% Lysine pH 6.3 | 109% | 58% | 52% | 52% |
| NDV Suc/1% Lysine PH 6.6 | 49% | 49% | 51% | 35% |
| NDV Suc/1% Lysine PH 7.3 | 72% | 85% | 64% | 62% |
| NDV Suc/1% Lysine PH 8.3 | 89% | 68% | 74% | 58% |
| NDV Suc/1% Lysine PH 8.8 | 69% | 64% | TNTC | 64% |

TNTC: Too numerous to count

Example 12

Stability of NDV in Different Sucrose Concentrations

NDV was prepared by methods described in example 1 and buffer exchanged into a 10% (w/v) sucrose. Test samples of NDV at different concentration of sucrose solution were prepared by adding different concentrated sucrose or by adding water for injection and stored at −20° C. The final titers of each formulation were adjusted to approximately 2E10. Stability samples were tested by plaque assay as described in example 1. The results indicate that the virus prepared in 10 to 20% (w/v) sucrose was more stable than virus prepared in lower concentrations of sucrose.

TABLE XI

Sucrose concentration effect on the NDV stability at −20° C.

| Formulation | % Activity Remaining | |
|---|---|---|
| | 6 Month | 9 Month |
| NDV 2.5% (w/v) Sucrose | 63% | 51% |
| NDV 5.0% (w/v) Sucrose | 67% | 76% |
| NDV 7.5% (w/v) Sucrose | 60% | 55% |
| NDV 10% (w/v) Sucrose | 100% | 84% |
| NDV 15% (w/v) Sucrose | 81% | 71% |
| NDV 20% (w/v) Sucrose | 89% | 83% |

What is claimed is:

1. A method for preserving stability of an enveloped virus, comprising storing the virus in aqueous solution for six months or longer at a temperature from −4° C. to −30° C., wherein the aqueous solution consists essentially of:
   the enveloped virus at a concentration of from $10^6$ PFU/mL to $10^{12}$ PFU/mL;
   and a non-reducing saccharide,
      wherein the saccharide is a disaccharide and is present in the solution at a concentration of from 5% (w/v) to 50% (w/v) or a monosaccharide and is present in the solution at a concentration of from 2.5% (w/v) to 25% (w/v);
   wherein the solution
      has an osmotic pressure of about 250 mOs or higher;
      has a pH of from 5 to 10;
      contains less than 0.1% (w/v) Sodium chloride;
      and contains substantially no glutamate or phosphate.

2. The method of claim 1, wherein the solution further comprises an amino acid selected from lysine or arginine at a concentration from 0.1% (w/v) to 5% (w/v) or lysine and arginine at a combined concentration from 0.1% (w/v) to 5% (w/v).

3. A method for preserving stability of an enveloped virus, comprising storing the virus in aqueous solution for six months or longer at a temperature from −4° C. to −30° C., wherein the aqueous solution comprises:
   an enveloped virus at a concentration of from $10^6$ PFU/mL to $10^{12}$ PFU/mL;
   and a non-reducing saccharide,
      wherein the saccharide is a disaccharide and is present in the solution at a concentration of from 5% (w/v) to 50% (w/v) or a monosaccharide and is present in the solution at a concentration of from 2.5% (w/v) to 25% (w/v);
   wherein the solution
      has an osmotic pressure of about 250 mOs or higher;
      has a pH of from 5 to 10;
      and contains
         substantially no reducing agents antioxidants, glutamate, or phosphate,
         and less than:
            0.1% (w/v) Sodium chloride;
            1% (w/v) Dextran;
            0.5% (w/v) Mannitol;
            0.1% (w/v) Sorbitol;
            0.01% (w/v) Polysorbate;
            0.5% (w/v) polyethylene glycol;
            0.1 mM Calcium chloride;
            0.5% (w/v) Phosphatidyl choline;
            0.05% (w/v) Glycine.

4. The method of claim 3, wherein the solution contains substantially no Sodium chloride, Dextran, Mannitol, Sorbitol, Polysorbate, polyethylene glycol, Calcium chloride, Phosphatidyl choline, and Glycine.

5. The method of claim 3, wherein the solution further comprises an amino acid selected from lysine or arginine at a concentration from 0.1% (w/v) to 5% (w/v) or lysine and arginine at a combined concentration from 0.1% (w/v) to 5% (w/v).

6. The method of claim 5, wherein the concentration of lysine and/or arginine is about 1% (w/v).

7. The method of claim 3, wherein the storage temperature is about −20° C.

8. The method of claim 3, wherein the virus is a paramyxovirus.

9. The method of claim 8, wherein the virus is a Newcastle disease virus.

10. The method of claim 3, wherein the virus concentration is from $1 \times 10^{10}$ PFU/mL to $7 \times 10^{10}$ PFU/mL.

11. The method of claim 3, wherein the disaccharide concentration is from 7.5% (w/v) to 15% (w/v).

12. The method of claim 11, wherein the disaccharide concentration is from about 10% (w/v) to about 20% (w/v).

13. The method of claim 3, wherein the saccharide is sucrose.

14. The method of claim 3, wherein the saccharide is trehalose.

15. The method of claim 3, wherein the monosaccharide concentration is from 4% (w/v) to 7% (w/v).

16. The method of claim 15, wherein the monosaccharide concentration is about 5% (w/v).

17. The method of claim 3, wherein the osmotic pressure is about 300 mOs.

18. The method of claim 3, wherein the pH is from 7 to 9.

19. The method of claim 3, wherein the solution is sterile.

20. The method of claim 3, wherein the enveloped virus is a Newcastle disease virus and the saccharide is sucrose at a concentration from about 10% (w/v) to about 20% (w/v).

21. The method of claim 5, wherein the enveloped virus is a Newcastle disease virus, the saccharide is sucrose at a concentration from about 10% (w/v) to about 20% (w/v), and the amino acid is Lysine at a concentration of about 1% (w/v).

* * * * *